United States Patent
Brown

[11] Patent Number: 5,835,884
[45] Date of Patent: Nov. 10, 1998

[54] METHOD OF DETERMINING A CHARACTERISTIC OF A FLUID

[76] Inventor: Alvin E. Brown, 134 Oak Knoll Dr., Santa Cruz, Calif. 95060

[21] Appl. No.: 720,789

[22] Filed: Oct. 4, 1996

[51] Int. Cl.$^6$ .................................................. G01F 1/708

[52] U.S. Cl. ................................. 702/45; 702/46; 702/48; 73/861.27; 73/861.28; 73/861.02; 73/861.03

[58] Field of Search ............................... 364/510, 464.23, 364/422, 506, 509, 484, 486, 487, 524, 550, 551.01, 556, 557, 558, 565, 569, 575, 577, 580, 723, 803, 804, 853, 528.16, 528.17; 73/54.01, 861.27–861.29, 861.31, 861, 597, 861.02, 861.03, 861.05, 861.18, 861.25, 861.42, 1.34, 1.35, 1.16, 1.83, 152.18, 152.21, 152.29, 195, 196, 862.29, 204.11, 204.14, 204.19; 340/606, 618, 616, 603; 367/25–27, 21; 377/20, 21; 181/400–402, 29.6; 702/45–48, 50, 51, 54, 55, 103

[56] References Cited

U.S. PATENT DOCUMENTS

| Re. 28,929 | 8/1976 | Brown | 73/861.28 |
| 3,817,098 | 6/1974 | Brown | 73/861.28 |
| 4,331,025 | 5/1982 | Ord, Jr. | 73/54.01 |
| 4,748,857 | 6/1988 | Nakagawa | 73/861.28 |
| 4,754,641 | 7/1988 | Orban et al. | 73/152.21 |
| 5,458,004 | 10/1995 | van der Pol | 73/861.29 |
| 5,639,972 | 6/1997 | Hastings et al. | 73/862.29 |

*Primary Examiner*—Hal O. Wachsman
*Attorney, Agent, or Firm*—Richard W. Hanes

[57] ABSTRACT

A method of determining a characteristic of a fluid involves measuring a sonic transit time (102), along a non-perpendicular path, through the fluid. The sonic transit time is used to determine a speed of sound in the fluid (104). A measured flow rate (106) is determined from the sonic transit time. A friction factor (108) is calculated using the speed of sound and the measured flow rate. Next, a velocity profile (110) is determined using the friction factor. Finally, an adjusted flow rate is calculated (112) using the velocity profile.

20 Claims, 6 Drawing Sheets

METHOD OF DETERMINING A CHARACTERISTIC OF A FLUID

FIELD OF THE INVENTION

The present invention relates generally to the field of flow meters and more specifically to a method of determining a characteristic of a fluid.

BACKGROUND OF THE INVENTION

Ultrasonic flow meters have many advantages over other methods of determining flow rates. Ultrasonic flow meters can continuously measure the flow rate, while other methods generally measure average flow rates. In addition, ultrasonic flow meters are obstructionless and work with non-conductive fluids.

Ultrasonic flow meters have a pair of transducers that are placed on either side of the flow path of a fluid flowing through a pipe. The transducers are pointed at each other and the line between them has a component in the direction of the fluid flow. The principle used to detect flow rates is that the wavelength of an ultrasonic packet will lengthen in the upstream and shorten in the downstream path. The amount by which the wavelength changes is directly proportional to the flow rate. Unfortunately, the flow rate across the pipe is not uniform. This means that what is really measured by the ultrasonic meter is the line integral fluid speed (measured flow speed). Multiplying the measured flow speed by the area of the pipe to find the volume flow speed gives erroneous results. Generally, a fudge factor or a heuristic relationship is used to adjust to the measured flow speed, before multiplying by the pipe area to determine the volume flow speed. These methods of adjusting the measured flow speed have proved unsatisfactory.

Thus there exists a need for a method that can accurately convert the measure flow speed (line integral fluid speed) to the average (by area) flow speed and therefore correctly determine the volume flow speed.

SUMMARY OF THE INVENTION

A method that overcomes these and other problems involves measuring a sonic transit time, along a non-perpendicular path, through the fluid. The sonic transit time is used to determine a speed of sound in the fluid. A measured flow rate is determined from the sonic transit time. A friction factor is calculated using the speed of sound and the measured flow rate. Next, a velocity profile is determined using the friction factor. Finally, an adjusted flow rate is calculated using the velocity profile.

DETAILED DESCRIPTION OF THE DRAWINGS

Figure 1:
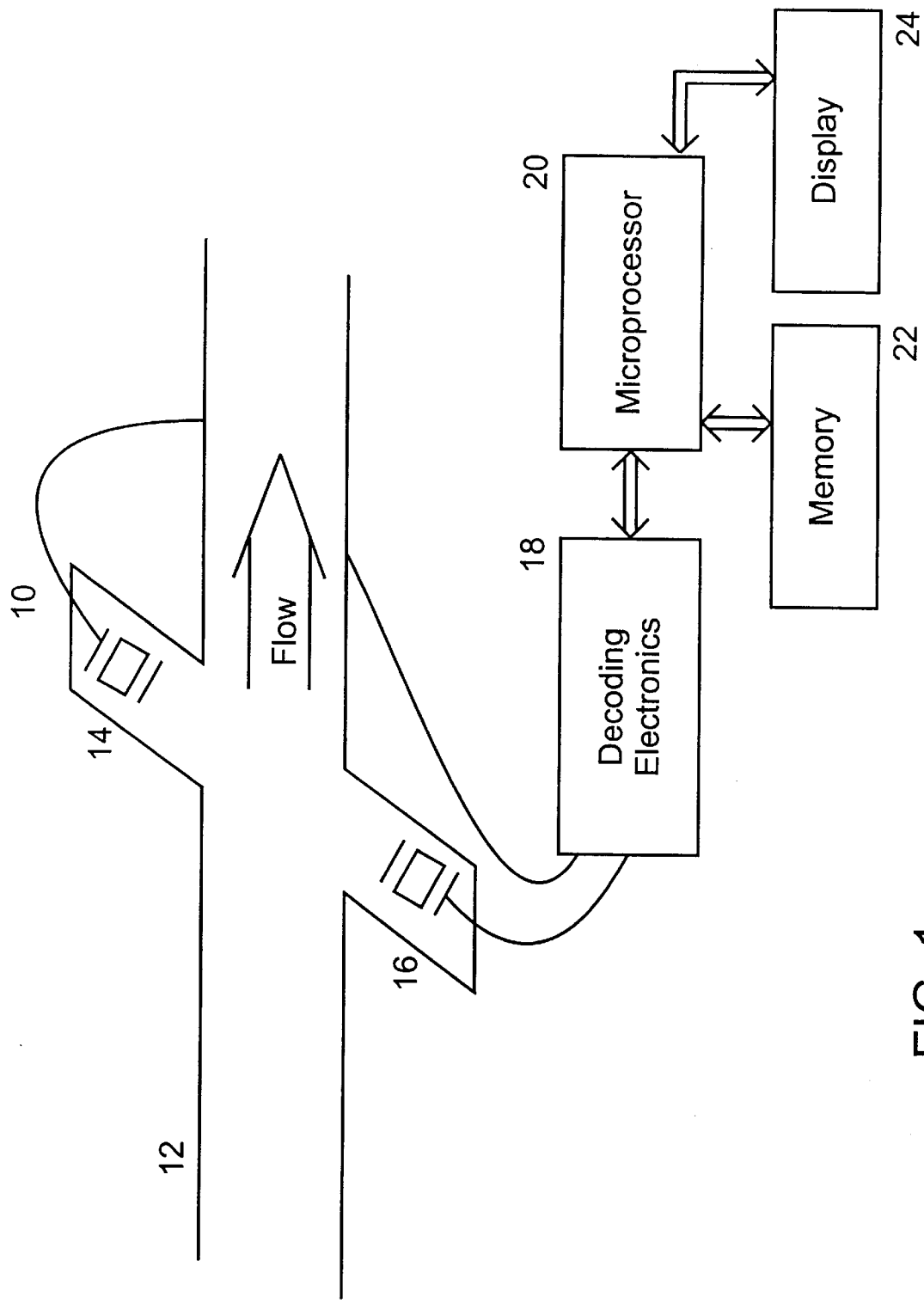
FIG. 1 is a block diagram of an ultrasonic flow meter.

FIG. 1 is a block diagram of an ultrasonic flow meter 10 attached to a pipe 12. A fluid is flowing in the pipe 12. The ultrasonic flow meter 10 has a pair of transducers 14, 16 that emit and receive ultrasonic pulses. The ultrasonic pulses travel along a path that is non-perpendicular (non-perpendicular path) to the direction of flow of the fluid. The pair of transducers 14, 16 send and receive signals from a decoding electronics 18. The decoding electronics determine an upstream sonic speed and a downstream sonic speed. These sonic speeds are used by a microprocessor 20 to determine a speed of sound in the fluid and a measured flow rate. In addition, the microprocessor controls the decoding electronics and calculates a temperature, a viscosity, a head loss, a density, a volume flow rate of the fluid. The microprocessor 20 is connected to a memory (computer-readable storage medium) 22. The memory 22 contains computer-readable instructions that can be executed by the microprocessor 20. The memory 12 can be a ROM (Read Only Memory), a RAM (Random Access Memory), a CD-ROM (Compact Disk-Read Only Memory), a diskette or any other computer readable storage medium. In one embodiment the microprocessor 20 is coupled to a display 24. The display 24 is used to display a characteristic (e.g., temperature, volume flow rate) of the fluid flowing in the pipe 12.

Figure 2:
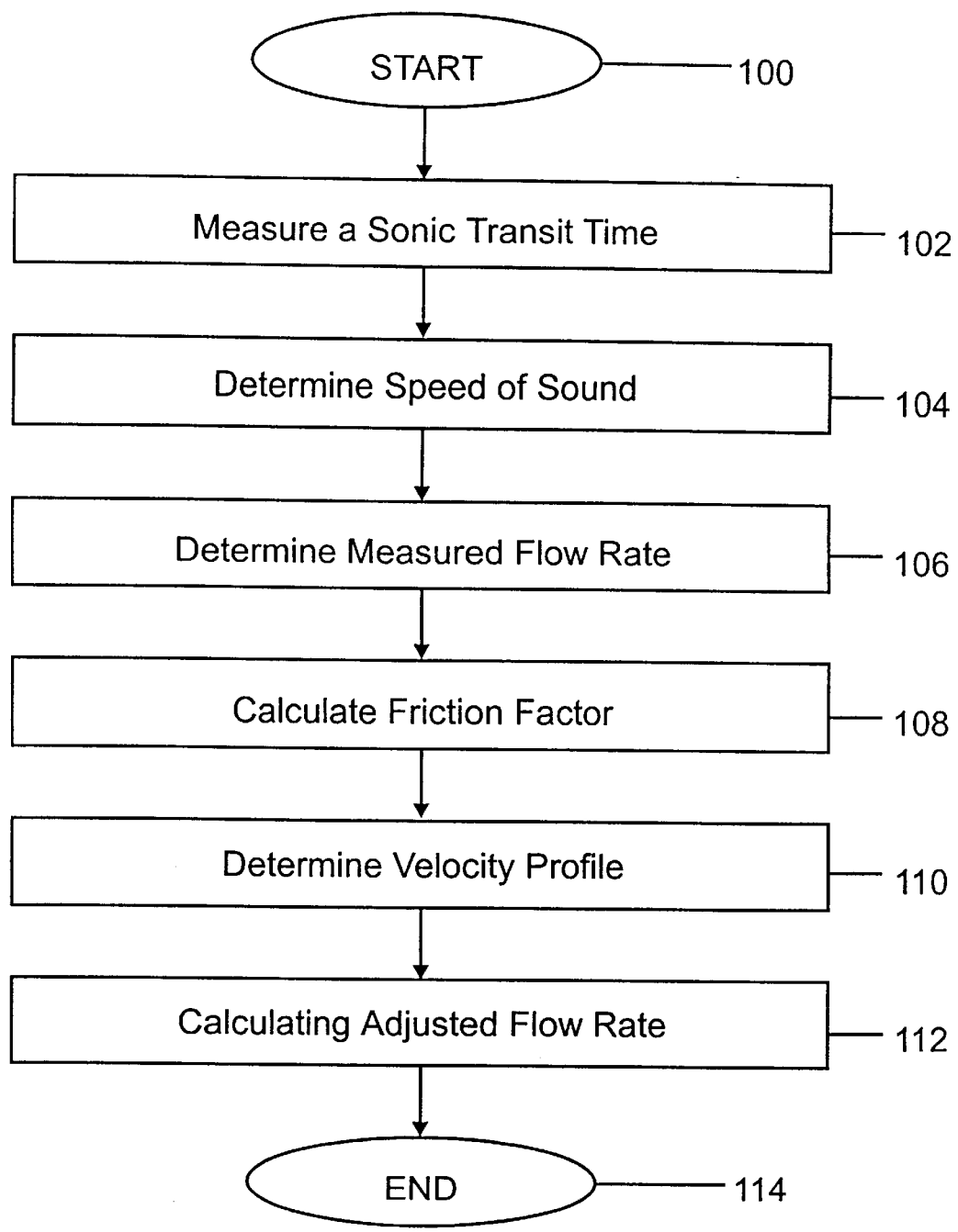
FIG. 2 is a flow chart of a process for determining an adjusted flow rate.

A process, executable by a computer (microprocessor), to determine an adjusted flow rate is shown in FIG. 2. The process starts, step 100, by measuring a sonic transit time in both the upstream and the downstream paths at step 102. A speed of sound in the fluid is determined using the sonic transit times at step 104. A measured flow rate (line integral fluid speed) of the fluid is determined at step 106. Next a friction factor is calculated at step 108, using the speed of sound and the measured flow rate. The friction factor allows one to determine a velocity profile of the fluid at step 110. A velocity profile shows the velocity of the fluid at any point along a radial line inside the pipe. Using this knowledge one can integrate the velocity per unit area to determine an adjusted flow rate. However, there are equations that give the average flow rate, by volume, for a given velocity profile. Multiplying the average flow rate (adjusted flow rate) by the area or the pipe gives the correct volume flow rate of the fluid. At step 112, the adjusted flow rate is calculated and the process ends at step 114.

Figure 3:
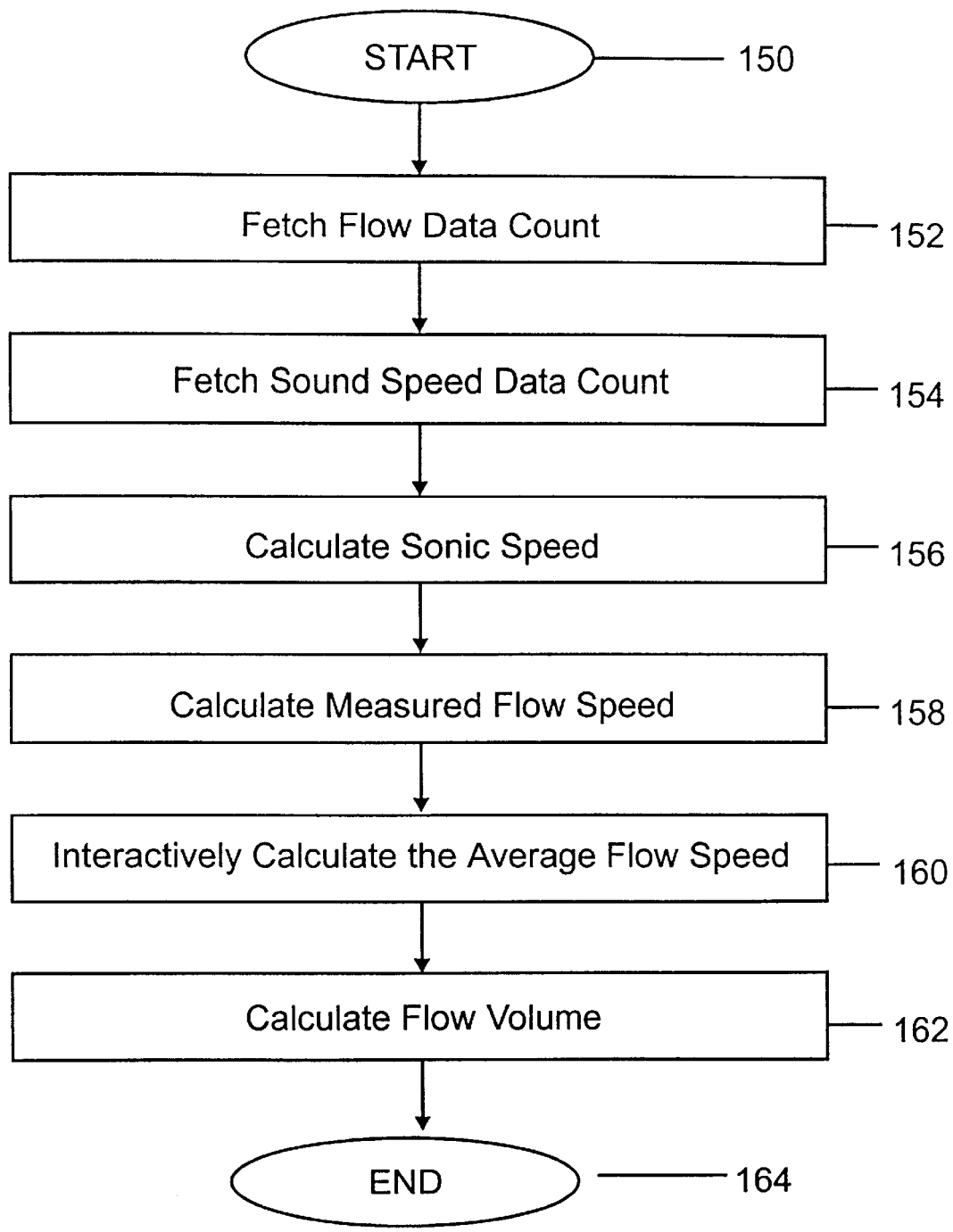
FIG. 3 is a flow chart of a process of determining a flow volume.

FIG. 3 is a flow chart of the process to determine the flow volume of a liquid. The process starts, step 150, by fetching a flow data count at step 152. The flow data count is the difference frequency between an upstream frequency and a downstream frequency. The upstream frequency is defined as the frequency at which one period of the upstream signal is equal to the upstream transit time between the transducers. The downstream frequency is similarly defined. Next the sound speed data count is fetched at step 154. The sound speed data count is the sum frequency between the upstream frequency and the downstream frequency. A sonic speed (speed of sound) is calculated using the sound speed data count at step 156. A standard look up table for every fluid relates the speed of sound in the fluid to a density, a viscosity and a temperature of the fluid. A measured flow speed is calculated using the flow data count at step 158. An average flow speed is iteratively calculated at step 160. The process of iteratively calculating the average flow speed is explained in more detail in FIG. 4. From the average flow speed, the flow volume is calculated at step 162, which ends the process at step 164.

Figure 4:
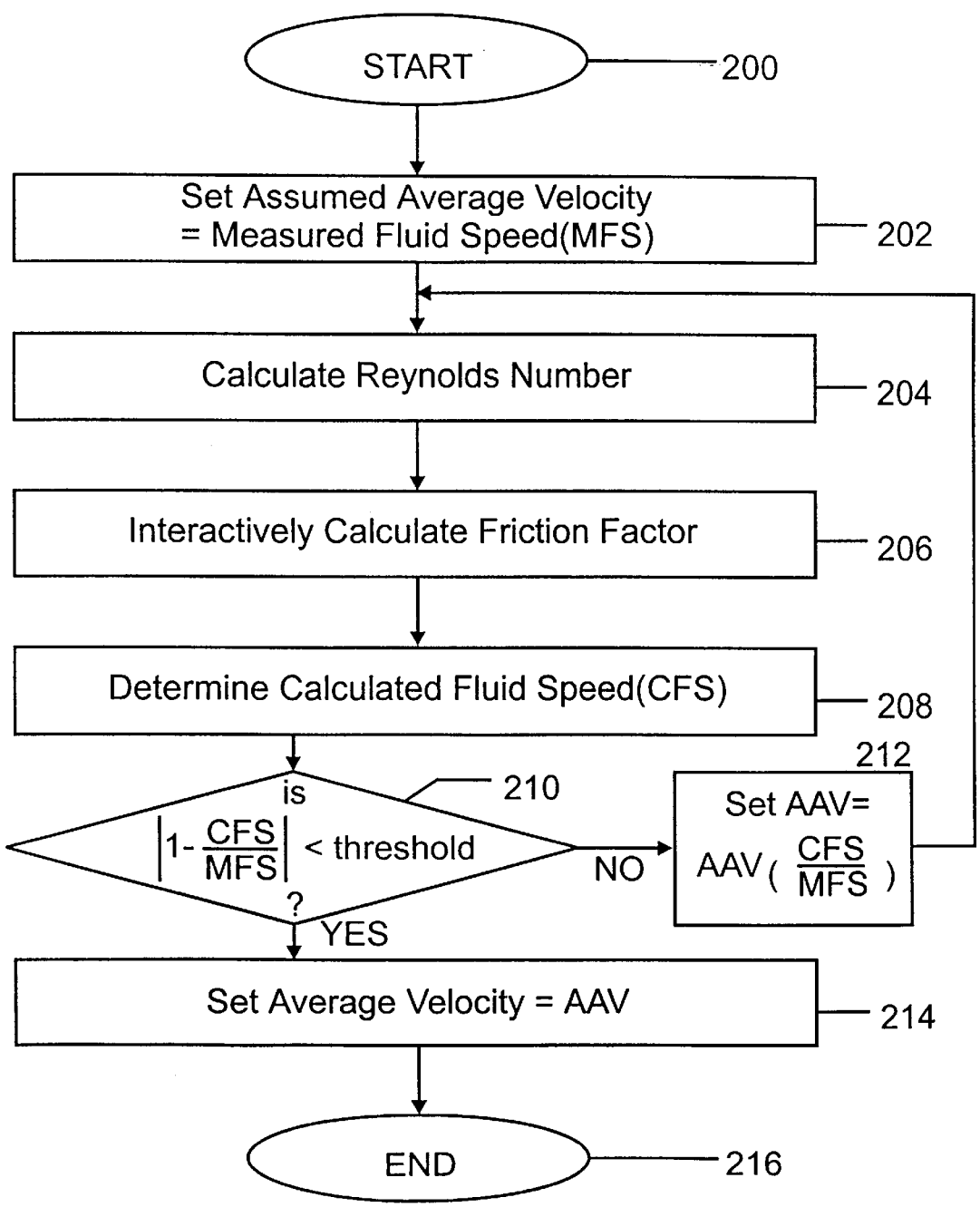
FIG. 4 is a flow chart of a process for determining an average flow speed.

FIG. 4 is flow chart of the iterative process of determining the average velocity (by volume) of the fluid in the pipe. The process starts, step 200, by setting an assumed average velocity equal to the measured flow speed (MFS, measured fluid speed) at step 202. A Reynolds number is calculated using the assumed average velocity, the density of the fluid and the viscosity of the fluid at step 204. Next the friction factor is iteratively calculated at step 206. The process of iteratively calculating the friction factor is explained in more detail in conjunction with FIG. 6. A calculated fluid speed is determined at step 208. The process of determining the calculated fluid speed (CFS) is explained in more detail in conjunction with FIG. 5. The ratio of the calculated fluid speed to the measured fluid speed is compared to a predetermined range at step 210. When the ratio is outside the predetermined range, adjusting the assumed average velocity by the ratio at step 212. Then returning to step 204. When the ratio is within (or equal to) the predetermined range, setting the average velocity equal to the assumed average velocity at step 214 and ending the process at step 216.

Figure 5:
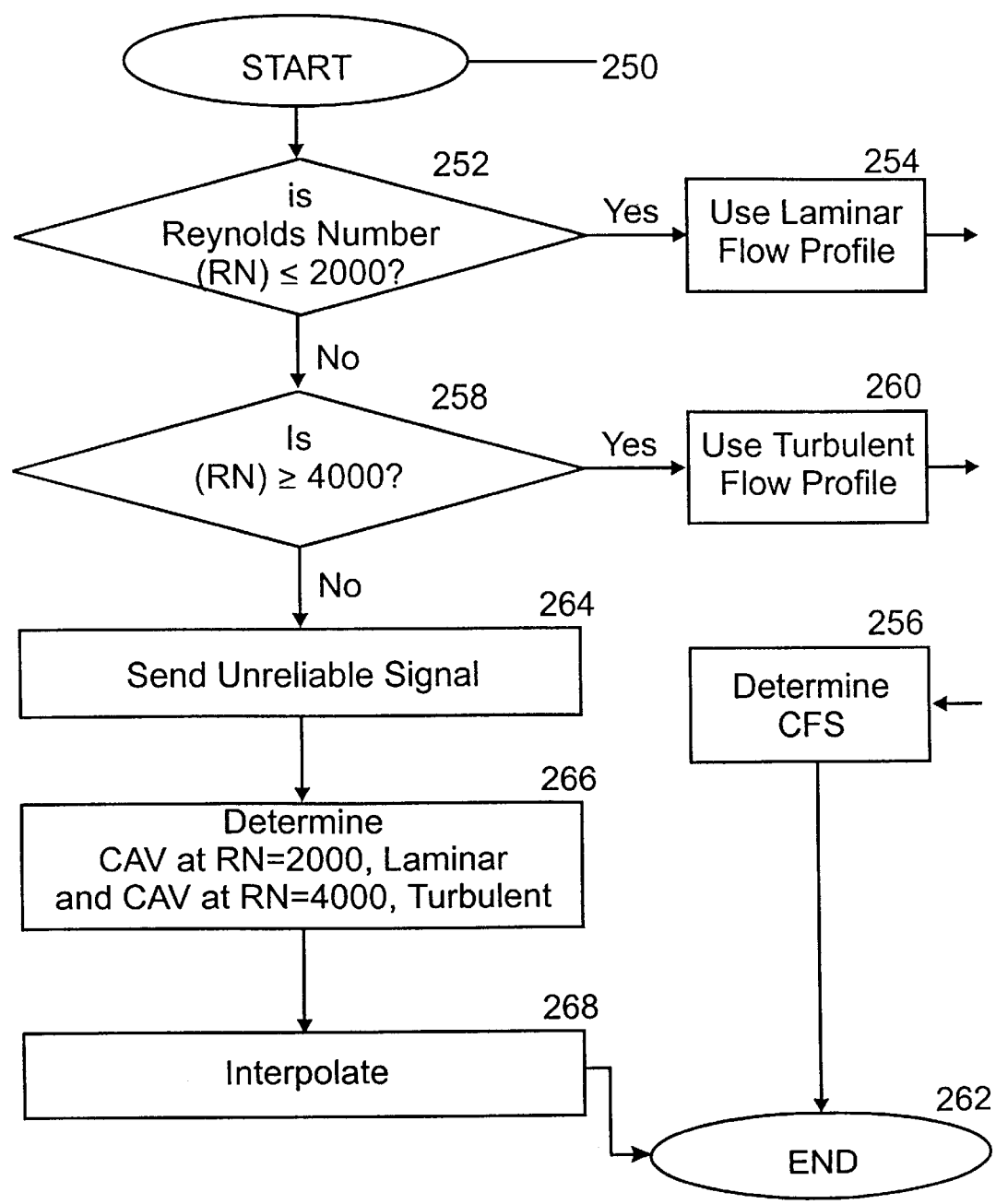
FIG. 5 is a flow chart of a process of determining a calculated fluid speed.

FIG. 5 is a flow chart of the process of determining the calculated fluid speed. The process starts, step 250, by determining if the Reynolds number is less than or equal 2000, at step 252. When the Reynolds number is less than or equal to 2000 using a Laminar flow velocity profile at step 254. The calculated fluid speed is determined at step 256.

When the Reynolds number is greater than 2000, it is determined if the Reynolds number is greater than or equal to 4000 at step 258. When the Reynolds number is greater than or equal to 4000, using a turbulent flow velocity profile at step 260. Then determining the calculated fluid velocity at step 256 and ending at step 262.

When the Reynolds number is between 2000 and 4000, sending an unreliable signal (unreliable indicator signal) at step 264. Next, determine the calculated average velocity (Laminar flow rate) at a Reynolds number of 2000 using the Laminar flow velocity profile and determine the calculated average velocity (turbulent flow rate) at a Reynolds number of 4000 using the turbulent flow velocity profile at step 266. Interpolate between the Laminar flow rate and the turbulent flow rate using the Reynolds number at step 268. In the preferred embodiment the interpolation is a logarithmic interpolation process.

Figure 6:
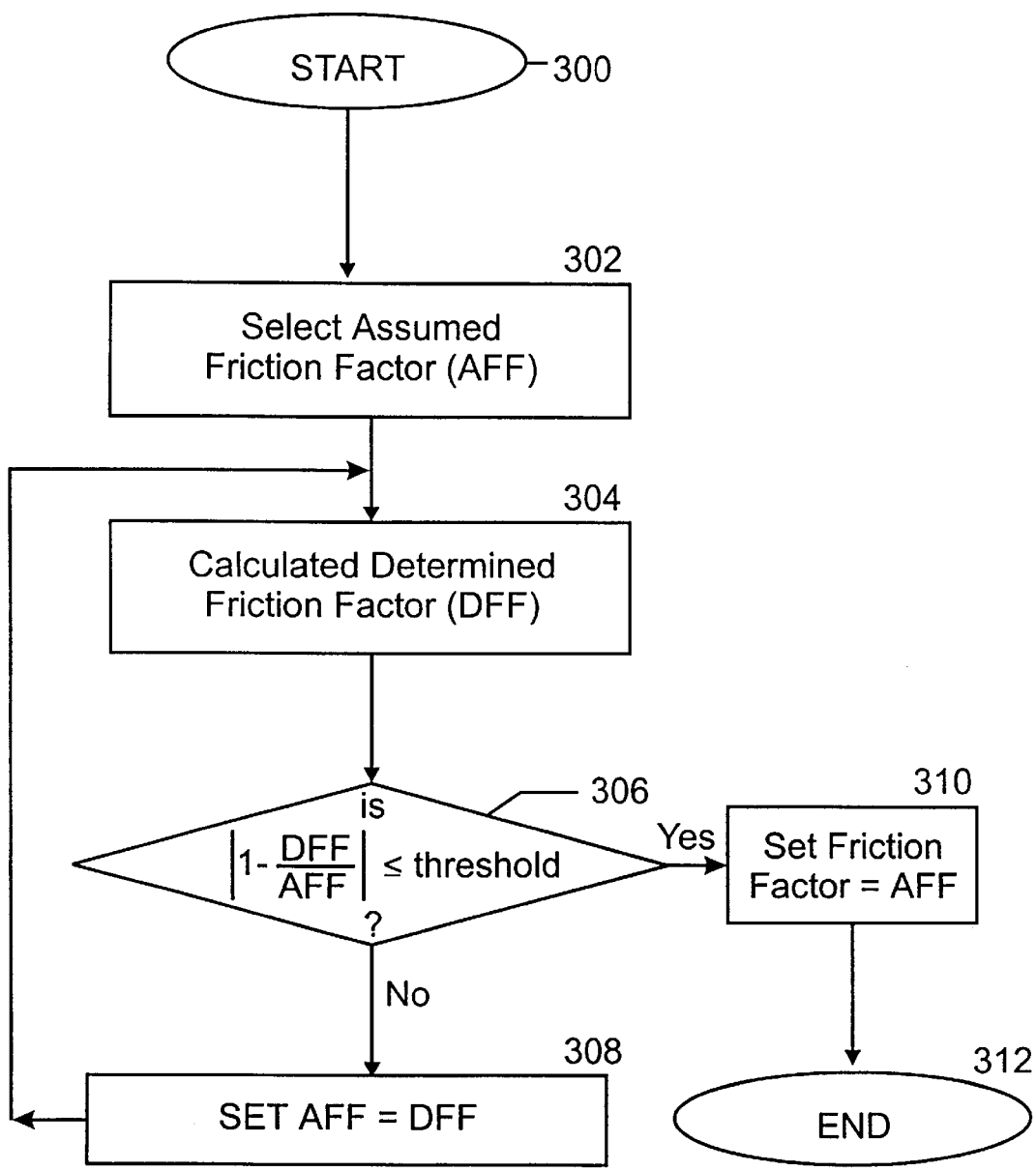
FIG. 6 is a flow chart of a process of determining a friction factor.

FIG. 6 is a flow chart of the process of determining a friction factor. The process starts, step 300, by selecting an assumed friction factor at step 302. In one embodiment the initial assumed friction factor is set equal to 0.032. Next a determined friction factor (DFF) is calculated at step 304 using a pipe diameter. At step 306, it is determined if the friction ratio between the predetermined friction factor and the assumed friction factor is less than a predetermined friction range. In one embodiment it is determined if the absolute value of one minus the friction ratio is less one part per million. When the friction ratio is not between the predetermined friction factor, setting the assumed friction factor equal to the determined friction factor at step 308. When the friction ratio is between the predetermined friction factor, setting the friction factor equal to the assumed friction factor at step 310, which ends the process at step 312. Knowing the friction factor the head loss through the flow meter can be calculated. This information is important for axial meters.

The above processes accurately determines the volume flow rate from the measured flow rate and does not use fudge factors. In addition, the process accurately determines the fluid temperature, fluid density, fluid viscosity, head loss and the speed of sound in the fluid flowing in the pipe. While the invention has been described in conjunction with specific embodiments thereof, it is evident that many alterations, modifications, and variations will be apparent to those skilled in the art in light of the foregoing description. Accordingly, it is intended to embrace all such alterations, modifications, and variations in the appended claims.

What is claimed is:

1. A method of determining a characteristic of a fluid flowing through a pipe, comprising the steps of:

(a) measuring a sonic transit time, along a non-perpendicular path, through the fluid;

(b) determining a speed of sound in the fluid from the sonic transit time;

(c) determining a measured flow rate from the sonic transit time;

(d) calculating a friction factor using the speed of sound in the fluid and the measured flow rate;

(e) determining a velocity profile using the friction factor; and (f) calculating an adjusted flow rate using the velocity profile.

2. The method of claim 1, further including the steps of:

(g) calculating a head loss.

3. The method of claim 1, wherein step (d) further includes the steps of:

(d1) determining a fluid temperature using the speed of sound;

(d2) determining a fluid viscosity using the fluid temperature;

(d3) calculating a Reynolds number using the measured flow rate and the fluid viscosity.

4. The method of claim 3, wherein step (e) further includes the steps of:

(e1) when the Reynolds number is less than or equal to 2000, using a Laminar flow velocity profile;

(e2) when the Reynolds number is greater than or equal to 4000, using a turbulent flow velocity profile.

5. The method of claim 4, further including the step of:

(e3) when the Reynolds number is between 2000 and 4000, sending an unreliable indicator signal.

6. The method of claim 5, further including the steps of:

(e4) calculating a Laminar flow rate at the. Reynolds number of 2000;

(e5) calculating a turbulent flow rate at the Reynolds number of 4000;

(e6) determining the adjusted flow rate by interpolating between the Laminar flow rate and the turbulent flow rate, using the Reynolds number.

7. A method of determining a characteristic of a fluid flowing through a pipe, comprising the steps of:

(a) measuring a sonic transit time;

(b) calculating a sonic speed and a measured fluid speed, using the sonic transit time;

(c) setting an assumed average velocity equal to the measured fluid speed;

(d) calculating a Reynolds number using the assumed average velocity;

(e) calculating a friction factor using the Reynolds number and a pipe diameter;

(f) calculating a calculated fluid speed, using the friction factor;

(g) comparing the calculated fluid speed to the measured fluid speed to form a ratio;

(h) when the ratio is within a predetermined range, calculating a flow volume, using the assumed average velocity.

8. The method of claim 7, further including the steps of:
(i) when the ratio is outside the predetermined range, correcting the assumed average velocity by the ratio of the calculated fluid speed to the measured fluid speed;
(j) returning to step (d).

9. The method of claim 7, wherein step (f) further includes the steps of:
(f1) when the Reynolds number is less than or equal to 2000, using a Laminar flow velocity profile;
(f2) when the Reynolds number is greater than or equal to 4000, using a turbulent flow velocity profile.

10. The method of claim 7, wherein step (b) further includes the step of determining a temperature of the fluid.

11. The method of claim 10, wherein step (b) further includes the step of determining a density of the fluid.

12. The method of claim 7, wherein step (b) further includes the step of determining a viscosity of the fluid.

13. The method of claim 7, wherein step (e) further includes the steps of:
(e1) selecting an assumed friction factor;
(e2) calculating a determined friction factor, using the assumed friction factor and the Reynolds number;
(e3) comparing the assumed friction factor to the determined friction factor, to form a friction ratio;
(e4) when the friction ratio is within a predetermined friction range, setting the friction factor to the assumed friction factor.

14. The method of claim 13, further including the steps of:
(e5) when the friction ratio is outside the predetermined friction range, setting the assumed friction factor equal to the determined friction factor;
(e6) returning to step (e2).

15. A computer-readable storage medium containing computer-readable information for calculating the flow volume of a fluid through a conduit that when executed by a computer performs the following steps:
(a) fetching a flow data count of the fluid from decoding electronics for ultrasonic flow meter transducers;
(b) fetching a sound speed data count of the fluid from decoding electronics for ultrasonic flow meter transducers;
(c) calculating a sonic speed using the sound speed count;
(d) calculating a measured fluid speed using the flow data count;
(e) iteratively calculating an average fluid speed, using the measured fluid speed and the sonic speed; and
(f) calculating the flow volume using the average fluid speed.

16. The computer-readable storage medium of claim 15, wherein step (e) further includes the steps of:
(e1) setting an assumed average velocity equal to the measured fluid speed;
(e2) calculating a Reynolds number using the assumed average velocity;
(e3) calculating a friction factor using the Reynolds number and a pipe diameter;
(e4) calculating a calculated fluid speed, using the friction factor;
(e5) comparing the calculated fluid speed to the measured fluid speed to form a ratio;
(e6) when the ratio is within a predetermined range, calculating a flow volume, using the assumed average velocity.

17. The computer-readable storage medium of claim 16, further including the steps of:
(e7) when the ratio is outside the predetermined range, correcting the assumed average velocity by the ratio of the calculated fluid speed to the measured fluid speed;
(e8) returning to step (e2).

18. The computer-readable storage medium of claim 16, wherein step (e4) further includes the steps of:
(i) when the Reynolds number is less than or equal to 2000, using a Laminar flow velocity profile;
(ii) when the Reynolds number is greater than or equal to 4000, using a turbulent flow velocity profile.

19. The computer-readable storage medium of claim 18, further including the step of:
(iii) when the Reynolds number is between 2000 and 4000, sending an unreliable indicator signal.

20. The computer-readable storage medium of claim 19, further including the step of:
(iv) calculating a Laminar flow rate at the Reynolds number of 2000;
(v) calculating a turbulent flow rate at the Reynolds number of 4000;
(vi) determining the adjusted flow rate by interpolating between the Laminar flow rate and the turbulent flow rate, using the Reynolds number.

* * * * *